(12) United States Patent
Lindner et al.

(10) Patent No.: US 9,610,107 B2
(45) Date of Patent: Apr. 4, 2017

(54) ROD INSERTION INSTRUMENT

(71) Applicant: Aesculap AG, Tuttlingen (DE)

(72) Inventors: Stephan Lindner, Wurmlingen (DE); Peyman Pakzaban, Houston, TX (US)

(73) Assignee: Aesculap AG (DE)

( * ) Notice: Subject to any disclaimer, the term of this patent is extended or adjusted under 35 U.S.C. 154(b) by 229 days.

(21) Appl. No.: 14/326,769

(22) Filed: Jul. 9, 2014

(65) Prior Publication Data
US 2015/0018892 A1    Jan. 15, 2015

(30) Foreign Application Priority Data
Jul. 10, 2013 (DE) .................. 10 2013 107 308

(51) Int. Cl.
*A61B 17/70* (2006.01)

(52) U.S. Cl.
CPC ...... *A61B 17/7086* (2013.01); *A61B 17/7083* (2013.01); *A61B 17/7088* (2013.01); *A61B 17/7089* (2013.01)

(58) Field of Classification Search
CPC .................................. A61B 17/7083–17/7089
USPC ...................................................... 606/86 A
See application file for complete search history.

(56) References Cited

U.S. PATENT DOCUMENTS

| | | | |
|---|---|---|---|
| 6,379,356 B1* | 4/2002 | Jackson ............ | A61B 17/7091 606/270 |
| 2008/0154280 A1 | 6/2008 | Schumacher | |
| 2009/0105774 A1 | 4/2009 | Jones | |
| 2010/0004701 A1* | 1/2010 | Malandain ......... | A61B 17/0485 606/86 R |
| 2011/0022088 A1* | 1/2011 | Forton ............... | A61B 17/7089 606/246 |
| 2011/0313475 A1 | 12/2011 | McLean | |
| 2012/0022594 A1 | 1/2012 | Walker | |

FOREIGN PATENT DOCUMENTS

| | | |
|---|---|---|
| DE | 102011053295 A1 | 3/2013 |
| EP | 2305154 A1 | 4/2011 |
| EP | 2353530 A1 | 8/2011 |
| WO | 2007025132 A2 | 3/2007 |

(Continued)

OTHER PUBLICATIONS

Aesculap Implant Systems, "S[4]® MIS Cannulated Pedicle Screw System", p. 7 (2010).

(Continued)

*Primary Examiner* — Nicholas Plionis
(74) *Attorney, Agent, or Firm* — RatnerPrestia (57) ABSTRACT

Described is a rod insertion instrument for the insertion of a fixation rod in the tulips of adjacent pedicle screws in the context of a dorsal spinal column stabilization. It has a grip portion, a tube section adjoining it and a gripping head carried by the tube section, in which gripping head the fixation rod is rotationally fixedly and angularly stably receivable with its proximal end. In order to minimize accidental tissue compression during the fixing of the fixation rod into the pedicle screws, the gripping head is attached to the tube section exclusively via a lockable joint with which there is enabled an unconstrained pivoting movement of the tube section toward the fixation rod during the process of fixing the fixation rod to the pedicle screw.

17 Claims, 5 Drawing Sheets

(56) References Cited

FOREIGN PATENT DOCUMENTS

WO    2011143550 A1    11/2011

OTHER PUBLICATIONS

B Braun, "Aesculap S$^4$® Spinal System FRI", pp. 15 and 26 (published prior to Jul. 10, 2013; date of publication not available).
German Search Report with partial translation issued in related German Application No. 10 2013 107 308.5, dated Feb. 11, 2014.

* cited by examiner

ROD INSERTION INSTRUMENT

RELATED APPLICATIONS

This application claims the benefit of priority under 35 U.S.C. §119 of German Application No. DE 10 2013 107 308.5, filed Jul. 10, 2013, the content of which is incorporated by reference herein in its entirety and for all purposes.

FIELD

The invention relates to a rod insertion instrument for inserting a fixation rod into the tulips of adjacent pedicle screws in the context of a dorsal spinal column stabilization.

BACKGROUND

Dorsal spinal column stabilization by means of a screws/rod system involves inserting the fixation rod as gently as possible into the tulip of pre-set adjacent pedicle screws. A variety of approaches for the design of such rod insertion instruments are known.

In the case of the rod insertion instrument according to EP 2 353 530 A1, a gripping head for the fixation rod sits over a pin on a central inner shaft of the instrument, on which a displaceable sleeve is guided, with which displaceable sleeve a pivoting of the gripping head about 90° via a handle arrangement is possible. In order to introduce the fixation rod, this is initially brought into a position in which it is oriented essentially parallel to the inner shaft. Subsequently the gripping head is pivoted about approximately 90° by actuation of the sleeve by using the handle arrangement, whereupon the fixation rod is navigated into the tulips of the pedicle screws.

The stability of this known rod insertion instrument is relatively limited due to the transmission configuration required for this system.

In order to provide more stable connections to the fixation rod, it is known to directly pivotably fix the fixation rod onto the rod insertion instrument. These solutions are shown for example from documents EP 2 305 154 A1, WO 2007/025132 A2 or US 2011/0313475 A1. The problem of these known rod insertion instruments however lies in the fact that the orientation of the fixation rod during insertion is often not sufficiently exactly controllable.

Finally a rod insertion instrument has become known from document WO 2011/143550 A1, whereby the fixation rod is adjustable and is fixable at the distal end of the rod insertion instrument. However this arrangement requires a relatively complex design of the proximal end of the fixation rod and of the corresponding complementary surfaces on the rod insertion instrument.

A generic rod insertion instrument is distributed by the Applicant AESCULAP AG under the product code FW 240 R. With this rod insertion instrument the insertion of the fixation rod takes place with a fixed angular position assignment between fixation rod and tube section. In this way, it is possible to introduce the fixation rod with good control and also minimally invasively or percutaneously into the body. In order to provide a good angular position for rod insertion, the gripping head is marginally angled with respect to the tube section within the order of magnitude of approximately 30° such that the fixation rod accommodated in the gripping head, during insertion into the tulips of the adjacent pedicle screws, includes an obtuse angle with the axis of the tube section of approximately 120°. While this fixedly set angular position between rod insertion instrument and fixation rod is also advantageous for the handling of the instrument, this design however also brings with it the problem that during screwing in of the so-called 'set screws' into the pedicle screws for fixing the fixation rod, over-stressing of the soft tissue in the region of the adjacent skin incision can often occur.

SUMMARY

Therefore the invention is based on the object of developing a rod insertion instrument in such a way that punctual over-stressing of the soft tissue is effectively avoided while retaining a very stable connection between rod insertion instrument and fixation rod, and while retaining also good and controlled guidability of the fixation rod during minimally invasive or percutaneous insertion of the fixation rod in the body.

This object is achieved through a rod insertion instrument for the insertion of a fixation rod into the tulips of adjacent pedicle screws in the context of a dorsal spinal column stabilization. The rod insertion instrument has a grip portion, a tube section adjoining it and a gripping head carried by the tube section in which the fixation rod is rotationally fixedly and angularly stably receivable with its proximal end, wherein the connection between the fixation rod and the gripping head is releasable by means of a manually drivable sliding body. The gripping head is attached to the tube section exclusively via a lockable joint with which there is enabled an unconstrained pivoting movement of the tube section toward the fixation rod during the process of fixing the fixation rod to the pedicle screw.

The joint is formed from a hinge joint whose axis is essentially perpendicular to a plane spanned by the tube section and the fixation rod fixed in the gripping head.

The grip portion has at least one lateral flattened portion which is oriented essentially parallel to a plane spanned by the tube section and the fixation rod fixed in the gripping head.

The gripping head has the form of a two-armed pivot lever whose first lever arm, facing away from the tube section, has a prismatic polygonal recess for the accommodation of the fixation rod, and whose other lever arm, facing the tube section comprises on its end side at least one recess for the releasable engagement of a locking rod which is axially movable in the tube section.

Side surfaces of the gripping head on the side facing the tube section each comprise a recess such that the section remaining in between, in which the pivot axis is located, engages with form fit in a slot of the tube section, which passes perpendicular to the pivot axis, wherein both cheek walls of the tube section which border the slot preferably form a two-sided rotational limiting stop for the hinge joint, in cooperation with the recess of the gripping head.

One of the two cheek walls of the tube section, defining the slot, forms a rotation stop for the hinge joint in a first direction in cooperation with an associated cam surface of the recess on the relevant side surface of the gripping head, and the other cheek wall of the tube section forms a rotation stop for the hinge joint in the other direction, in cooperation with an associated cam surface of the recess on the other side surface of the gripping head.

The first lever arm is configured to be bent and accommodates in its bent lever arm section the manually drivable sliding body for the rotationally and angularly fixed clamping of the fixation rod in the prismatic polygonal recess.

The bent lever arm section is slightly angled, with respect to the lever arm facing the tube section, away from the extension direction of the fixation rod to be accommodated in the gripping head.

The locking rod is axially movable by means of an adjusting sleeve rotatably mounted in the grip portion, which adjusting sleeve forms at its one end a rotary handle and at its other end a polygonal recess for the form-locking functional engagement with an external polygon of the locking rod which with a threaded portion is in engagement with a counter thread of the tube section.

The locking rod is guided essentially over the entire length of the rod insertion instrument.

The adjusting sleeve for the locking and unlocking of the joint between tube section and gripping head is removable from the grip portion and is usable as an operating tool for the sliding body in the gripping head.

The sliding body in the gripping head is formed from a set screw having a polygonal head.

The sliding body continues, on the side facing the tube section, in a flexible guide rod on which the adjusting sleeve can be threaded.

The joint is lockable in a plurality of angular positions.

The rod insertion instrument can include a spring device with which, when the joint is unlocked, the pivoting motion of the tube section toward the fixation rod is supported.

The spring device is formed from a flexible guide rod which forms an extension of the sliding body on the side facing the tube section.

The tube section has lateral flattened portions which are oriented essentially parallel to a plane spanned by the tube section and the fixation rod fixed in the gripping head, and which give the tube section a width which corresponds essentially to the diameter of the fixation rod to be inserted with the rod insertion instrument, and thereby corresponds to the diameter of a circle which passes through the distal vertices of a polygonal recess of the gripping head.

According to the invention the gripping head is attached to the tube section exclusively, i.e. without further stabilizing means, via a lockable joint with which there is enabled an unconstrained pivoting movement, i.e. without any further kinematic constraints, of the tube section, toward the fixation rod, during the process of fixing the fixation rod to the pedicle screw. The invention is based on the following consideration: when in the case of an inserted fixation rod a so-called set screw is screwed into the pedicle screw, the fixation rod is at the same time pushed into the tulip and onto the screw head of the pedicle screw, whereby the gripping head and with it the tube section of the rod insertion instrument is subject to a pivoting movement. Thereby the tube section moves progressively nearer to the skin incision performed for the operation procedure. As soon as it touches the end of the skin incision, the joint which is unlocked in this state ensures that the tube section can orient itself, being more or less free of forces and free from any constraints and under support at the skin incision, without being pushed into the soft tissue. In this way it is possible to introduce the fixation rod into the body in a minimally invasively way, or percutaneously, with considerably smaller incisions, and to avoid tissue over-stressing, and indeed even when the joint is not actively controlled but rather operates purely passively due to the reaction forces which are exerted between body and rod insertion instrument. Therefore the rod insertion instrument according to the invention is suited especially to a surgical technique having an intramuscular entry.

In principle, it is possible to achieve the lockable joint in a variety of ways. A particularly robust and simple to manufacture configuration arises when the joint is formed from a hinge joint whose axis is essentially perpendicular to a plane spanned by the tube section and the fixation rod fixed in the gripping head. It is shown that a rod insertion instrument configured in this way can fulfil all requirements placed on a rod insertion instrument for the vast number of problems during spinal column stabilization by means of a screws/rod system. In addition the rod insertion instrument is very easily constructed and ensures a particularly high stability of the connection between rod insertion instrument and fixation rod, due to the simple hinge joint, whereby the navigating of the fixation rod is improved.

The grip portion has at least one lateral flattened portion which is oriented essentially parallel to a plane spanned by the tube section and the fixation rod fixed in the gripping head, as noted above. In this configuration, there arises a particularly good feel for the orientation of the fixation rod during insertion, whereby the manual operability is further improved.

As noted above, the gripping head has the form of a two-armed pivot lever whose first lever arm, facing away from the tube section, has a prismatic polygonal recess for the accommodation of the fixation rod, and whose other lever arm, facing the tube section comprises on its end side at least one recess for the releasable engagement of a locking rod which is axially movable in the tube section. Due to this configuration of the gripping head, relatively large stabilization forces for the hinge joint can be provided in the narrowest space.

Preferably the side surfaces of the gripping head each comprise a recess on the side facing the tube section such that the section remaining in between, in which the pivot axis of the joint is located, engages with form fit in a slot of the tube section running perpendicular to the pivot axis. In this case a rotational stop for the hinge joint can be provided by means of simple machining of the recesses and of the end surfaces of the cheek walls of the tube section, said cheek walls bordering the slot. Preferably this rotational stop is effective in two directions such that the gripping head obtains only a limited freedom of movement which facilitates the handling of the rod insertion instrument.

One of the two cheek walls of the tube section, defining the slot, forms a rotation stop for the hinge joint in a first direction in cooperation with an associated cam surface of the recess on the relevant side surface of the gripping head, and the other cheek wall of the tube section forms a rotation stop for the hinge joint in the other direction, in cooperation with an associated cam surface of the recess on the other side surface of the gripping head, as noted above. In this arrangement, the space required for the limiting of the pivoting movement is particularly well used, whereby each cheek wall is assigned a stopping (abutment) function for only one direction of rotation. In this way the abutments may be configured relatively stably within a small space.

When the first lever arm of the two-armed pivot lever is configured to be bent and it accommodates in its bent lever arm section the manually drivable sliding body for rotational and angular fixation of the fixation rod in the prismatic polygonal recess, there results the particular advantage that the drive of the sliding body can be provided laterally offset to the tube section of the rod insertion instrument. In this way no space problems occur with the design of the drive for the sliding body and with the drive of the locking rod for the hinge joint.

With the bent lever arm section slightly angled, with respect to the lever arm facing the tube section, away from the extension direction of the fixation rod to be accommodated in the gripping head, there arises a particularly favourable angular position between tube section and inserted fixation rod.

When the locking rod of the joint is axially movable by means of an adjusting sleeve rotatably mounted in the grip portion, which adjusting sleeve forms at its one end a rotary handle and at its other end a polygonal recess for the form-locking functional engagement with an external polygon of the locking rod which with a threaded portion is in engagement with a counter thread of the tube section, there arises a very space saving arrangement of the drive for the locking rod. It is shown that the drive thread may be executed without further development such that a few revolutions of the rotary handle and thereby of the adjusting sleeve are sufficient in order to provide the required stroke of the locking rod for locking and releasing the joint.

When the locking rod is guided essentially over the entire length of the rod insertion instrument, the particular advantage occurs that the locking rod may be executed with a small volume and made from a less strong material.

When the adjusting sleeve is removable from the grip portion and at the same time is usable as an operating tool for the sliding body in the gripping head, there arises a particularly simple construction of the rod insertion instrument. Here, in an advantageous manner, the circumstance is exploited that the sliding body in the gripping head need not occur simultaneously with the control of the hinge joint, rather only needs to be activated when the fixing of the fixation rod in the tulips of the pedicle screws is completed, such that a control of the joint between gripping head and tube section is no longer necessary.

When the sliding body continues, on the side facing the tube section, in a flexible guide rod on which the adjusting sleeve can be threaded, the rod insertion instrument is suited in particular to the minimally invasive or percutaneous insertion of the fixation rod. It is in any case ensured by means of the threading of the adjusting sleeve that the polygonal recess of the adjusting sleeve 'finds' the polygonal head of the set screw in the gripping head, even if this is concealed by the tissue.

The flexible guide rod may be executed corresponding to a particularly advantageous development, to give the joint a pre-loading with which, when the joint is unlocked, the pivoting motion of the tube section toward the fixation rod is supported. Of course such a preloading may be provided also by means of a differently designed spring device.

The tube section has lateral flattened portions which are oriented essentially parallel to a plane spanned by the tube section and the fixation rod fixed in the gripping head, and which give the tube section a width which corresponds essentially to the diameter of the fixation rod to be inserted with the rod insertion instrument, and thereby corresponds to the diameter of a circle which passes through the distal vertices of a polygonal recess of the gripping head, as noted above. When the rod insertion instrument is configured in this manner, the area of application of the rod insertion instrument is advantageously enhanced. With this design the rod insertion instrument can engage with lateral guidance into the longitudinal slot of a so-called 'down tube' or a push rod and/or a puller sleeve of a helping means fitted onto the pedicle screw, with which helping means a temporary or provisional fastening (locking) of the polyaxiality of the pedicle screw during insertion of the fixation rod is enabled. Such a helping means is for example subject of the German patent application DE 10 2011 053 295 A1 whose disclosed content is to be explicitly included in the present application.

BRIEF DESCRIPTION OF THE DRAWING FIGURES

An embodiment of the invention is explained in more detail with reference to schematic drawings.

FIGS. 9A to 9K shows schematic representations for clarifying the process of using the rod insertion instrument.

DETAILED DESCRIPTION

In the figures, a rod insertion instrument is indicated with the reference sign 10, with which a fixation rod can be inserted into the so-called tulips of adjacent pedicle screws by means of a screws/rod system in a minimally invasive or percutaneous way in the context of a dorsal spinal column stabilization. To clarify the insertion, FIG. 9 is now referred to, which shows the different phases of the insertion of a fixation rod 80 into the tulips of adjacent pedicle screws 82, 84.

The rod insertion instrument has a rod-shaped housing 12 having a grip portion 14 and a tube section 16 adjoining it. The handle body itself is indicated with 18.

Figure 2:
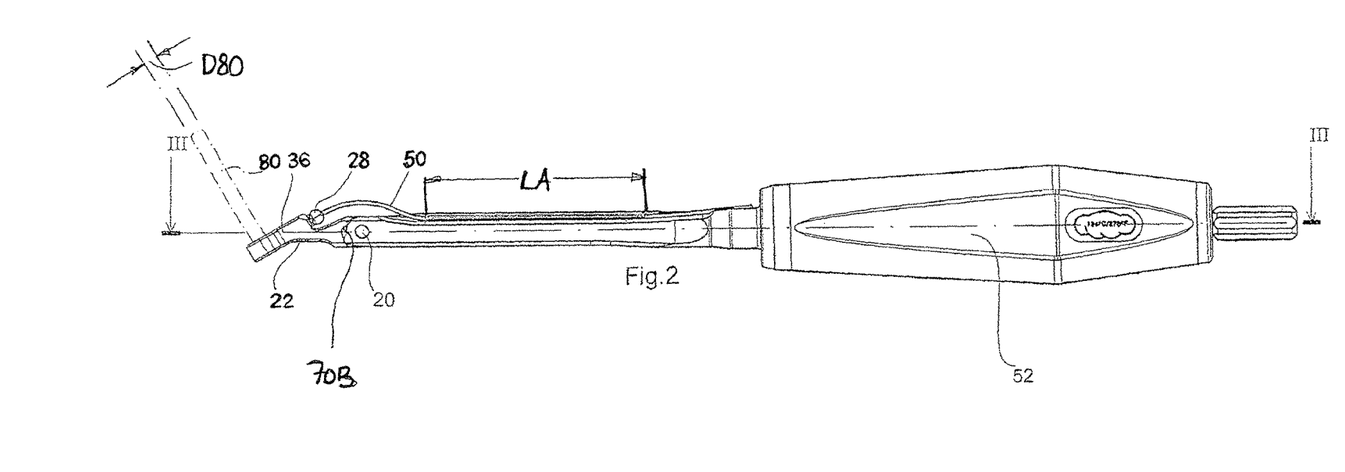
FIG. 2 shows a side view of the rod insertion instrument.
Figures 5, 5A:
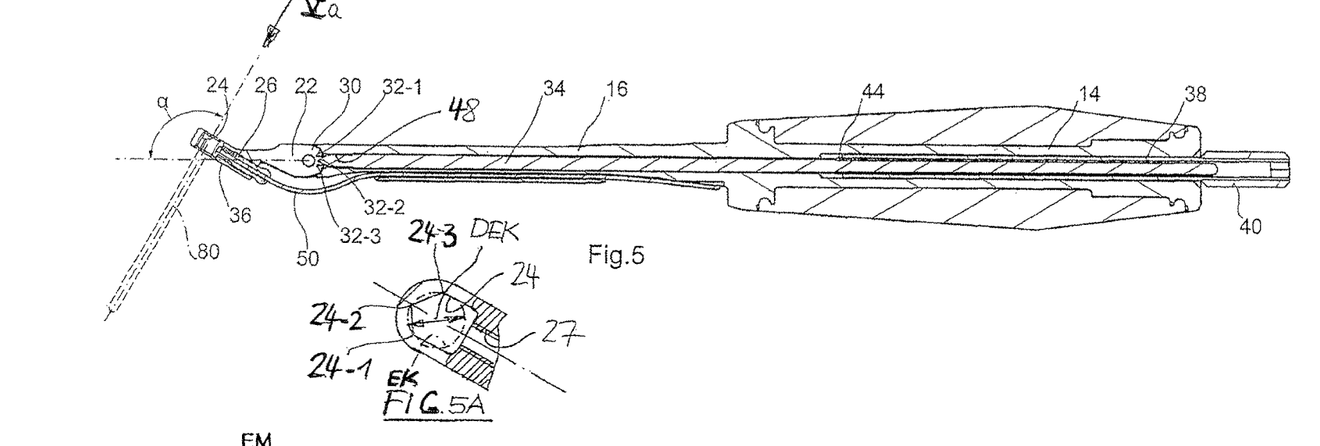
FIG. 5 shows a sectional view according to V-V in FIG. 4.
FIG. 5A shows a magnified view of a partially broken view of the gripping head when looking along 'Va' in FIG. 5.
Figure 6:
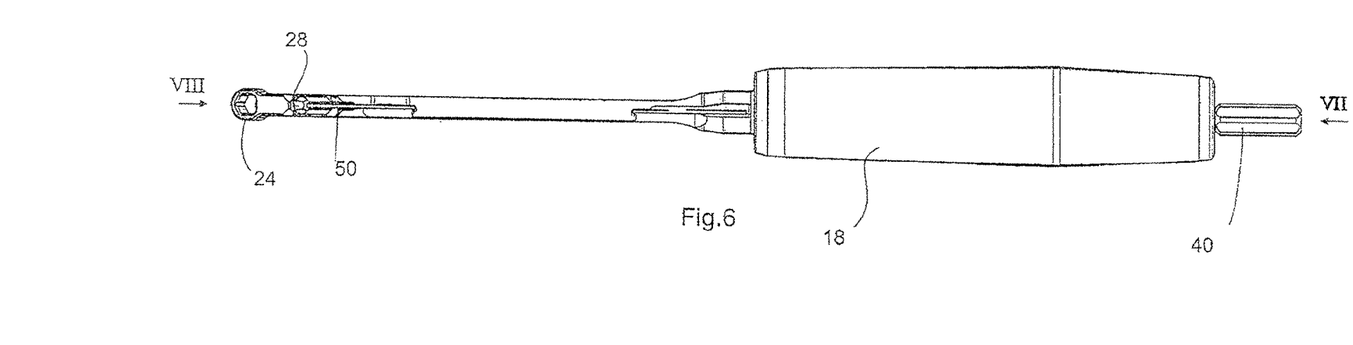
FIG. 6 shows a top view of the rod insertion instrument.
Figure 7:
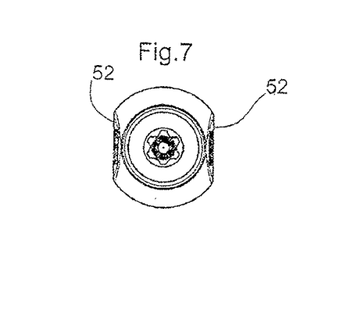
FIG. 7 shows the view according to 'VII' in FIG. 6.
Figure 8:
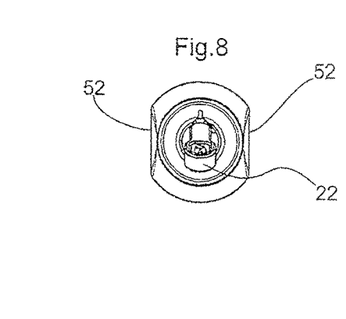
FIG. 8 shows the view according to 'VIII' in FIG. 6.

The tube section 16 carries a gripping head 22 via a joint pin 20, wherein the gripping head 22 comprises a prismatic polygonal recess 24—seen best in FIG. 5A—for the torsionally fixed accommodation of a polygonally configured proximal end section of a fixation rod 80 indicated with a dash-dotted line in FIG. 2. The fixation rod 80 having circular cross section and diameter D80 has for example a hexagonal section at its proximal end, wherein said hexagonal section is inscribed by the rod diameter D80 such that its greatest width essentially corresponds to the diameter D80. This hexagonal section is—as best seen in FIG. 5A—enclosed with a form-locking fit from four sides by the polygonal recess 24.

The proximal end of the fixation rod 80 thus has prismatic side surfaces (not further shown) which, when in the inserted state, bear on corresponding mating surfaces of the prismatic polygonal recess 24. As can be further seen from FIG. 5A, the prismatic polygonal recess 24 is configured such that the proximal end of the fixation rod 80 can be inserted with play in the polygonal recess 24. By means of a clamping screw indicated with 26, for which a thread 27 is provided in the gripping head 22 and is equipped with a polygonal screw head 28, the proximal end of the fixation rod having flattened sections can be pushed against the prism faces of the polygonal recess 24, whereby the fixation rod 80 can be rotationally and translationally fixed to the gripping head 22.

In FIG. 5A a circle EK is drawn in dash-dotted line, which passes through the three distal vertices 24-1, 24-2 and 24-3 of the polygonal recess 24 and which has a diameter DEK which essentially corresponds to the diameter D80 of the fixation rod to be inserted—with deviation of plus/minus 0.5 mm to 1 mm.

The arrangement is further provided that the tube section 16 is laterally flattened such that a width B 16 results which essentially corresponds to the dimension DEK of the circle EK. This flattened portion does not have a noticeable effect on the stability of the rod insertion instrument, since in this way the bending resistance moment in the plane decisive for the insertion process is not significantly smaller.

Figure 4:
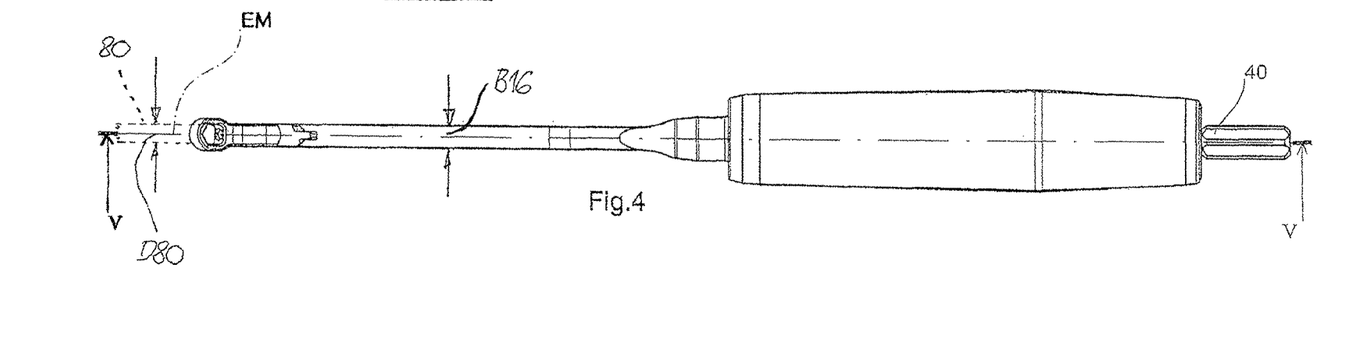
FIG. 4 shows a view of the rod insertion instrument from below.

From the view in FIG. 4, it is shown that the prismatic polygonal recess 24 is positioned such that it comes to lie symmetrical to the midplane EM of the rod insertion instrument.

The gripping head 22 has essentially the form of a two-armed pivot lever which is mounted via the joint pin 20 on cheek walls (not further shown) of the tube section 16 The distal lever arm forms the prismatic polygonal recess 24 for the accommodation of the fixation rod, while the other lever arm 30 facing the tube section 16 has three recesses 32-1 to 32-3 in which a locking rod 34 rotatably guided within the housing 12 can engage, in order to lock the joint formed from the joint pin 20 in three angular positions. The angular positions can be, for example, 0°, 15° or 30°.

The arrangement in the shown exemplary embodiment is provided such that the orientation of the fixation rod is at an angle α of 120° to the longitudinal axis of the rod insertion instrument—as shown in FIG. 5—for the case that the locking rod 34 engages in the central depression 32-2.

With the above described arrangement, the fixation rod can thus be rotationally fixedly and angularly stably accommodated in the gripping head 22, in order to be able to operate the rod insertion instrument in the same way as the generic rod insertion instrument which is currently marketed by the Applicant AESCULAP AG under the designation FW 240 R.

As is seen from FIGS. 2 and 5, the axis of the joint pin 20 is perpendicular to the plane EM spanned by the tube section 16 and the fixation rod 80 which is fixed in the gripping head 22, said plane coinciding with the drawing plane of FIG. 5.

As is most clearly seen from FIGS. 2 and 5, the lever arm of the gripping head 22 facing away from the tube section 16 is configured to be bent, wherein the bent lever arm section is indicated with 36. This lever arm section 36 accommodates the manually drivable sliding body in the form of the clamping screw 26 for the rotationally and angularly fixed clamping of the fixation rod 80 in the prismatic polygonal recess 24. Thereby there results in particular the advantage that the direction of movement of the sliding body, i.e. the clamping screw 26, does not coincide with the displacement direction of the locking rod 34.

As is further seen from the illustration according to FIG. 2 and FIG. 5, the bent lever arm section 36 is slightly angled (see FIG. 5), with respect to the lever arm 30 facing the tube section 16, away from the extension direction of the fixation rod 80 to be accommodated in the gripping head 22, wherein this angle is approximately 30° in the case of the shown embodiment.

Figure 3:
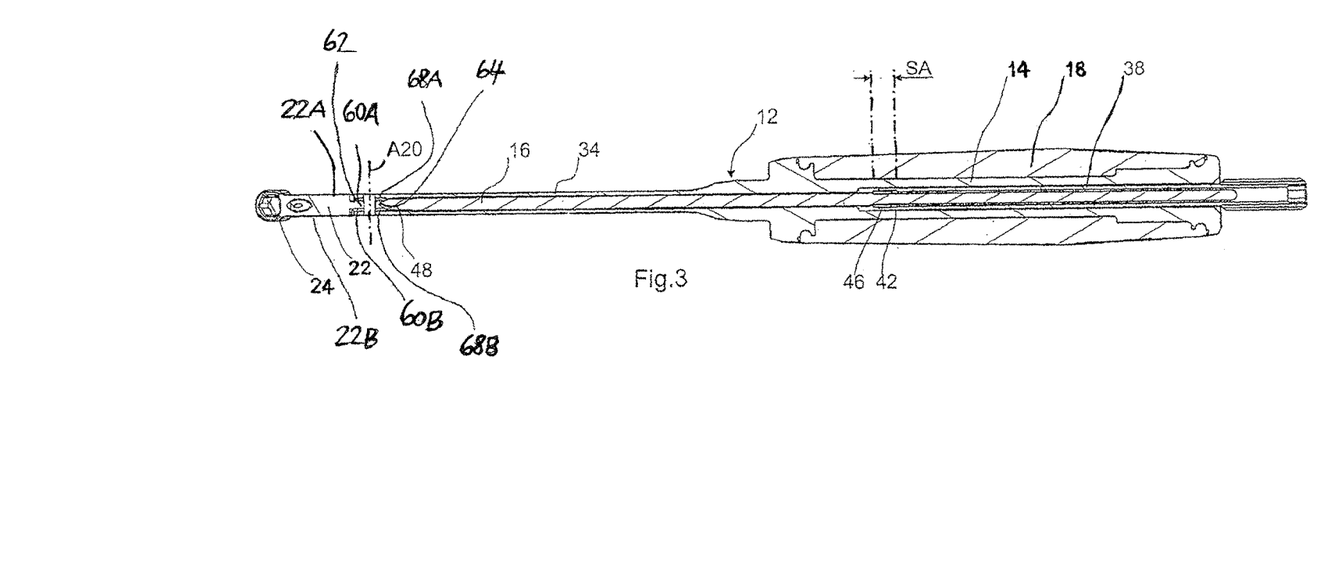
FIG. 3 shows the section according to in FIG. 2.

In order to be able to lock and release the hinge joint formed from the joint pin 20, the locking rod 34 is provided with a threaded portion 48 at its distal end, wherein said threaded portion 48 is in engagement with a thread (not shown in further detail) of the tube section 16. The locking rod 34 can be driven via a receivable adjusting sleeve 38 which is rotatably guided in the housing 12, in order to bring about the axial displacement of the locking rod 34. To this aim, the locking rod 34 rotationally fixedly carries an external polygon 46, for example an external hexagon which overlaps with a complementarily configured inner polygonal recess 42 of the adjusting sleeve 38 over a predetermined axial distance SA when the adjusting sleeve 38 is inserted in the housing 12—as shown in FIG. 3. The dimension SA is bigger than the required axial stroke of the locking rod 34, which is required for locking and unlocking of the joint 20.

In addition the hinge joint 20 has, in the embodiment shown, two limit stop positions that are realized in the following way:

As can be seen in FIGS. 2 and 4, side surfaces 22A, 22B of the gripping head 22 on the side facing the tube section 16 each comprise a recess 60A, 60B such that the section 62 remaining in between, in which the pivot axis A20 is located, engages with form fit in a slot 64 of the tube section 16, which passes perpendicular to the pivot axis A20. Both cheek walls 68A and 68B of the tube section 16 which border the slot 64 form a two-sided rotational stop for the hinge joint in cooperation with the recesses 60A, 60B of the gripping head 22.

In detail—as shown in FIGS. 2 and 3—the one cheek wall 68B of the tube section 16 forms a rotation stop for the hinge joint in a first direction in cooperation with an associated cam surface 70B of the recess 60B on the respective side surface 22B of the gripping head 22. The other cheek wall 68A of the tube section 16 forms a rotation stop for the hinge joint in the other direction, in cooperation with an associated—and not further indicated—cam surface of the recess 60A on the other side surface 22A of the gripping head 22.

The inner polygonal recess 42 is furthermore configured such that it can accommodate the polygonal head 28 of the clamping screw 26 with form fit. In this way the adjusting sleeve 38 is suited also as a tool for the actuation of the clamping screw 26.

Since the polygonal head 28 is located in the inside of the body and thus is concealed by tissue during the operation, it is difficult to accurately set the inner polygonal recess 42 on the polygonal head 28 without a helping means. Therefore the sliding body continues, on the side facing the tube section 16, in the form of the clamping screw 26 in a flexible guide rod 50 on which the adjusting sleeve 38 can be threaded for actuation of the clamping screw 26. Whilst the adjusting sleeve 38 is located in the housing 14, the free end of the flexible guide rod 50 is 'hidden' at the outer side of the tube section 16, as shown in FIGS. 1, 2, 5 and 6.

Figure 1:
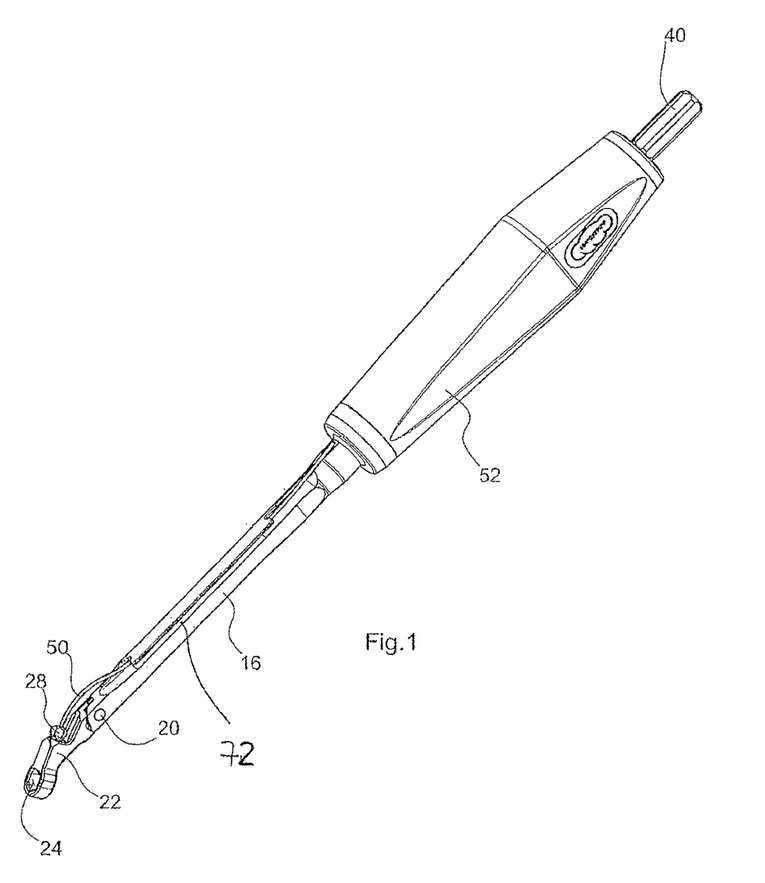
FIG. 1 shows a drawn-to-scale isometric view of the rod insertion instrument.

In the shown embodiment the guide rod 50 furthermore has the function of a spring device with which, when the joint is unlocked, the pivoting motion of the tube section 16 toward the fixation rod 80 is supported. In this case the guide rod 50 is configured as an elastically deformable or resilient rod which is receivable in a laterally open, preferably slightly undercut longitudinal pocket 72 and is displaceable in it over a predetermined axial length—as best shown in FIGS. 1, 2 and 5. In the relaxed state, i.e. in the extended condition of the elastic guide rod 50, the angle α which the inserted fixation rod 80 includes with the axis of the tube section 16, is minimum and the hinge joint is located in a first stop position. When the gripping head 22 is brought into an insertion position shown in the figures, the elastically bendable guide rod 50 is bent and spring-biased in the longitudinal pocket 72 under marginal axial movement. In this biased state of the guide rod, the hinge joint 20 is locked through actuation of the locking rod 34.

Finally it is clear from the illustrations according to FIGS. 1, 2, 7 and 8 that the grip portion 14 has lateral flattened portions 52 which are oriented such that they pass essentially parallel to a plane spanned by the tube section 16 and by the fixation rod 80 fixed in the gripping head 22. By means of these lateral gripping surfaces there arises a good feel for the orientation of the fixation rod to be inserted.

In the following the handling of the above-described rod insertion instrument is described with reference to FIGS. 9A to 9K.

After the pedicle screws 82, 84 are set, so-called 'down-tubes' or helping means (indicated with 90 and with dashed lines) are optionally attached, with which a temporary or provisional fastening (locking) of the polyaxiality of the pedicle screw is enabled during insertion of the fixation rod. Such helping means comprises for example a push rod and/or a puller sleeve fitted on the pedicle screw which is not described further, wherein a respective lateral longitudinal slot is configured in this helping means, said lateral longitudinal slot having an internal clearance essentially corresponding to the diameter of the fixation rod 80 to be placed. Such a helping means is for example subject of the German patent application DE 10 2011 053 295 A1 whose disclosed content is explicitly included in the present application.

After successful measurement and selection (length, curvature) of the required fixation rod 80, the selected fixation rod 80 is inserted into the prismatic polygonal recess 24 and fixed through actuation of the clamping screw 26—as shown in FIG. 5—under application of the adjusting sleeve 38. Subsequently the adjusting sleeve 38 can be inserted again into the grip portion 14. The guide rod is placed in the longitudinal pocket 72. Then the angle α (see FIG. 5) is appropriately selected while bending elastic deformation of the guide rod takes place, and the hinge joint 20 is locked into the relevant position while the locking rod is axially screwed in the relevant recess 32-1 to 32-3.

Figure 9A:
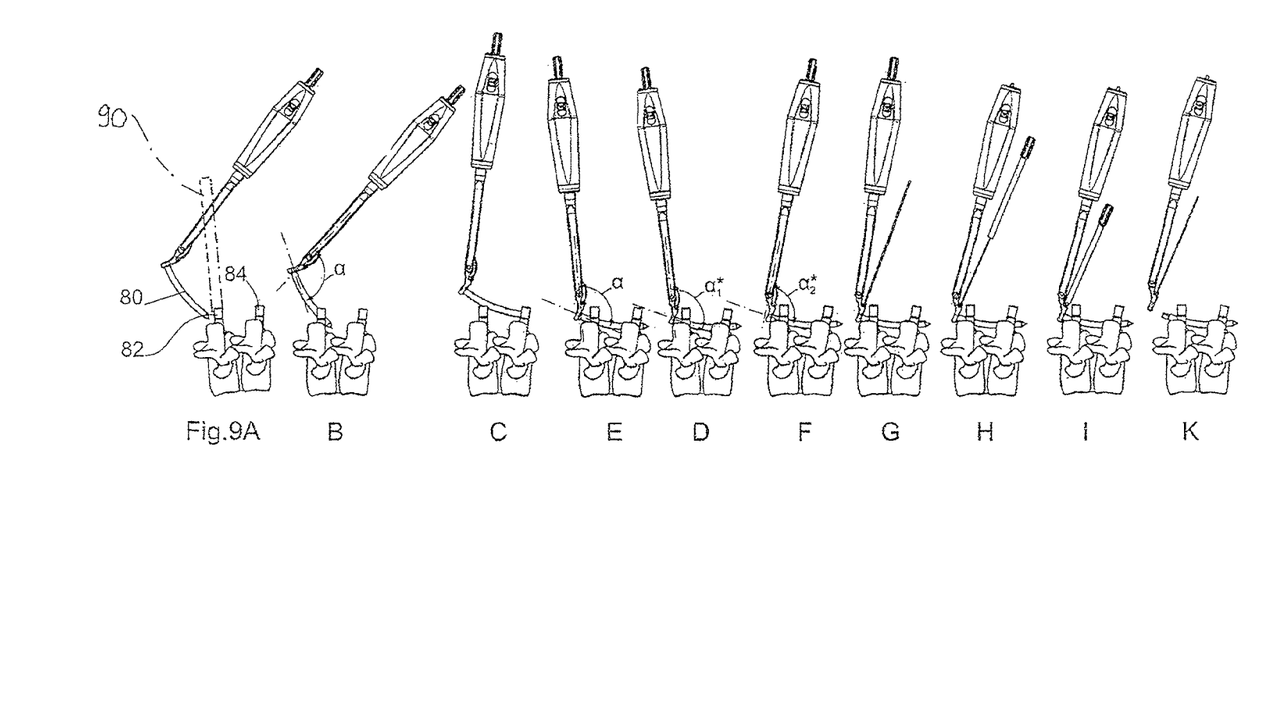

In this state one can begin with the insertion of the fixation rod 80—as shown in FIG. 9A. The fixation rod 80 is—as shown in FIGS. 9B and 9C—introduced into the aligned slots of the adjacent pedicle screws 82, 84, until it assumes the end position shown in FIG. 9D. The angle α between the orientation of the fixation rod 80 and the orientation of the tube section 16 remains thereby still unchanged. In this initial phase the rod insertion instrument, due to the width B16 adapted to suit the rod diameter D80, is optionally also laterally guided into the longitudinal slot of the so-called 'down tube' 90. The play here is preferably between 0.5 and 1 mm.

As shown in FIG. 9D, the fixation rod 80 in this phase of the insertion is still slightly inclined towards the orientation of the spinal column. Now before the so-called set-screws (not shown in detail) are screwed into the tulips of the pedicle screws 82, 84—in the phase according to FIG. 9E—the hinge joint 20 is unlocked through actuation of the adjusting sleeve 38 via the rotary handle, i.e. from the grip portion outwards, while the locking rod 34 is unscrewed from the corresponding recess 32-1 to 32-3. The arrangement is advantageously made such that only a small grip is required in order to bring about the required axial movement of the locking rod. In this functional position of the locking rod 34, the hinge joint 20 becomes a passive joint with the consequence that when the fixation rod 80—as shown in FIG. 9E—is pivoted to an orientation essentially parallel to the spinal column, the angle α* (see α*$_1$, α*$_2$) between the axis of the tube section 16 and the fixation rod 80 is simply reduced in such a way that the tube section 16 comes to rest at the skin incision and can then swing away from the skin incision without force. This pivoting motion of the tube section 16 is positively supported via the energy stored in the elastically bendable guide rod, while the guide rod attempts to take up its force-free extension position in the longitudinal pocket 72.

This swing movement which due to the passive configuration of the joint occurs constrained is indicated in FIGS. 9E and 9F. Upon definitive fixing of the fixation rod, the angle α*$_2$ is reduced to a value below 90°. Due to this resistance-free swing movement of the tube section 16, it is effectively excluded that punctual over-stressing of the tissue occurs in the area of the incision, whereby a substantial containment of the region traumatized by the operation is enabled.

In order now to separate the rod insertion instrument from the fixed fixation rod 80, the adjusting sleeve 38 is taken from the grip portion 14 and threaded onto the flexible guide rod 50 (see FIG. 9H), until the inner polygonal recess 42 engagingly reaches the screw head 28 of the clamping screw 26. The clamping screw 26 can thus be unscrewed from the bent section 36, whereby the fixation rod 80 is released. The released position is shown in FIG. 9K.

Of course deviations from the shown exemplary embodiment are possible, without departing from the principle of the invention. Thus in place of the described hinge joint, a multiaxial joint can also be used. The rod insertion instrument is of course also applicable to other forms of fixation rods, and also to all types of pedicle screws including polyaxial pedicle screws.

In place of an instrument construction having straight handle, an arrangement having offset-grip may be applied.

It should be emphasized at this point that in the configuration of the adjusting sleeve for the locking and unlocking of the hinge joint in such a form that it serves equally as operating tool for the clamping of the fixation rod in the gripping head, an independent invention is seen for which independent protection is claimed.

The invention thus provides a rod insertion instrument for the insertion of a fixation rod in the tulips of adjacent pedicle screws in the context of a dorsal spinal column stabilization. It has a grip portion, a tube section adjoining it and a gripping head carried by the tube section, in which gripping head the fixation rod is rotationally fixedly and angularly stably receivable with its proximal end. In order to minimize accidental tissue compression during the fixing of the fixation rod into the pedicle screws, the gripping head is attached to the tube section exclusively via a lockable joint with which there is enabled an unconstrained pivoting movement of the tube section toward the fixation rod during the process of fixing the fixation rod to the pedicle screw.

The invention claimed is:

1. A rod insertion instrument for the insertion of a fixation rod into tulips of adjacent pedicle screws in a context of a dorsal spinal column stabilization, the rod insertion instrument comprising:
    a grip portion,
    a tube section adjoining the grip portion,
    a gripping head carried by the tube section in which the fixation rod is rotationally fixedly and angularly stably receivable with its proximal end, and
    a locking rod,
    wherein a connection between the fixation rod and the gripping head is releasable by a manually drivable sliding body,
    wherein the gripping head is attached to the tube section exclusively via a lockable joint with which there is enabled a pivoting movement of the tube section toward the fixation rod during a process of fixing the fixation rod to the pedicle screw, the gripping head comprising a two-armed lever having a first lever arm and a second lever arm, where the first lever arm, facing the tube section, has a plurality of locking recesses formed in the first lever arm, the locking rod adapted to selectively engage the plurality of locking recesses to fix an orientation of the gripping head relative to the tube section in predetermined angles.

2. The rod insertion instrument according to claim 1, wherein the joint is formed from a hinge joint whose axis is perpendicular to a plane spanned by the tube section and the fixation rod fixed in the gripping head.

3. The rod insertion instrument according to claim 1, wherein the grip portion has at least one lateral flattened portion which is oriented parallel to a plane spanned by the tube section and the fixation rod fixed in the gripping head.

4. The rod insertion instrument according to claim 1, wherein the second lever arm, facing away from the tube section, has a prismatic polygonal recess for the accommodation of the fixation rod.

5. The rod insertion instrument according to claim 4, wherein side surfaces of the gripping head on the side facing the tube section each comprise a recess such that the section remaining in between, in which the pivot axis is located, engages with form fit in a slot of the tube section, which passes perpendicular to the pivot axis, the tube section comprising a first wall and a second wall, wherein the first wall and the second wall of the tube section border the slot and form a two-sided rotational limiting stop for the hinge joint, in cooperation with the recess of the gripping head.

6. The rod insertion instrument according to claim 5, wherein one of the first wall and the second wall of the tube section, defining the slot, forms a rotation stop for the hinge joint in a first direction in cooperation with an associated cam surface of the recess on the relevant side surface of the gripping head, and the other of the first wall and the second wall of the tube section forms a rotation stop for the hinge joint in the other direction, in cooperation with an associated cam surface of the recess on the other side surface of the gripping head.

7. The rod insertion instrument according to claim 4, wherein the first lever arm is configured to be bent and accommodates in its bent lever arm section the manually drivable sliding body for the rotationally and angularly fixed clamping of the fixation rod in the prismatic polygonal recess.

8. The rod insertion instrument according to claim 7, wherein the bent lever arm section is slightly angled, with respect to the lever arm facing the tube section, away from an extension direction of the fixation rod to be accommodated in the gripping head.

9. The rod insertion instrument according to claim 4, wherein the locking rod is axially movable by means of an adjusting sleeve rotatably mounted in the grip portion, which adjusting sleeve forms at its one end a rotary handle and at its other end a polygonal recess for the form-locking functional engagement with an external polygon of the locking rod which with a threaded portion is in engagement with a counter thread of the tube section.

10. The rod insertion instrument according to claim 9, wherein the locking rod is guided over the entire length of the rod insertion instrument.

11. The rod insertion instrument according to claim 9, wherein the adjusting sleeve for the locking and unlocking of the joint between the tube section and the gripping head is removable from the grip portion and is usable as an operating tool for the sliding body in the gripping head.

12. The rod insertion instrument according to claim 11, wherein the sliding body in the gripping head is formed from a set screw having a polygonal head.

13. The rod insertion instrument according to claim 12, wherein the sliding body, on the side facing the tube section, connects with a flexible guide rod on which the adjusting sleeve can be threaded.

14. The rod insertion instrument according to claim 1, wherein the joint is lockable in a plurality of angular positions.

15. The rod insertion instrument according to claim 1 comprising a spring device with which, when the joint is unlocked, the pivoting motion of the tube section toward the fixation rod is supported.

16. The rod insertion instrument according to claim 15, wherein the spring device is formed from a flexible guide rod which forms an extension of the sliding body on the side facing the tube section.

17. The rod insertion instrument according to claim 1, wherein the tube section has lateral flattened portions which are oriented parallel to a plane spanned by the tube section and the fixation rod fixed in the gripping head, and which give the tube section a width which corresponds to the diameter of the fixation rod to be inserted with the rod insertion instrument, and thereby corresponds to the diameter of a circle which passes through the distal vertices of a polygonal recess of the gripping head.

* * * * *